United States Patent [19]

Cianci et al.

[11] 4,140,127

[45] Feb. 20, 1979

[54] CATHETER ASSEMBLY

[75] Inventors: James P. Cianci, Cary; Frank K. Villari, Oak Park, both of Ill.

[73] Assignee: The Kendall Company, Boston, Mass.

[21] Appl. No.: 785,810

[22] Filed: Apr. 8, 1977

[51] Int. Cl.² ............................................. A61M 25/00
[52] U.S. Cl. .................................. 128/349 R; 206/364
[58] Field of Search ............ 128/349, 348, 350, 214.4, 128/263; 206/364, 363

[56] References Cited

U.S. PATENT DOCUMENTS

| 2,733,714 | 2/1956 | Haas | 128/263 |
|---|---|---|---|
| 2,947,415 | 8/1960 | Garth | 206/63.2 |
| 3,154,080 | 10/1964 | Rouan et al. | 128/349 |
| 3,930,580 | 1/1976 | Bazell et al. | 206/439 |
| 3,934,721 | 1/1976 | Juster | 128/349 R |
| 4,062,363 | 12/1977 | Bonner, Jr. | 128/348 X |

Primary Examiner—Stephen C. Pellegrino
Attorney, Agent, or Firm—Powell L. Sprunger

[57] ABSTRACT

A catheter assembly comprising, a catheter having an elongated shaft, and an elongated sleeve of flexible material covering at least a substantial portion of the catheter. The sleeve has a pair of opposed first and second walls extending between a pair of opposed longitudinal fold lines at sides of the sleeve with the catheter being received between the walls in a generally flat configuration of the sleeve. The sleeve has a circumferential cuff of enlarged dimensions defining an open distal end of the sleeve.

12 Claims, 10 Drawing Figures

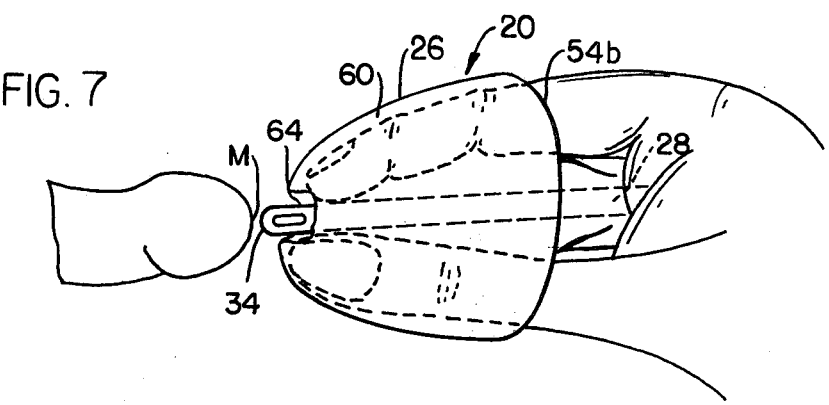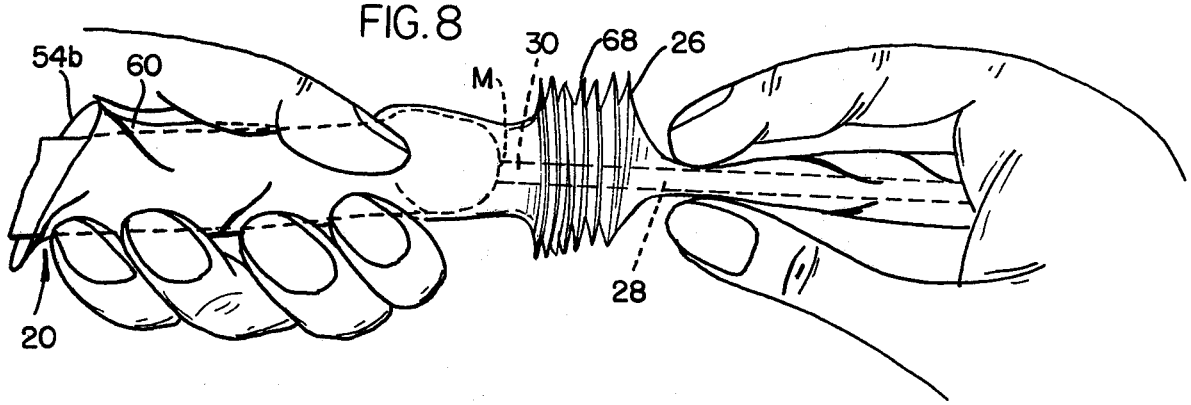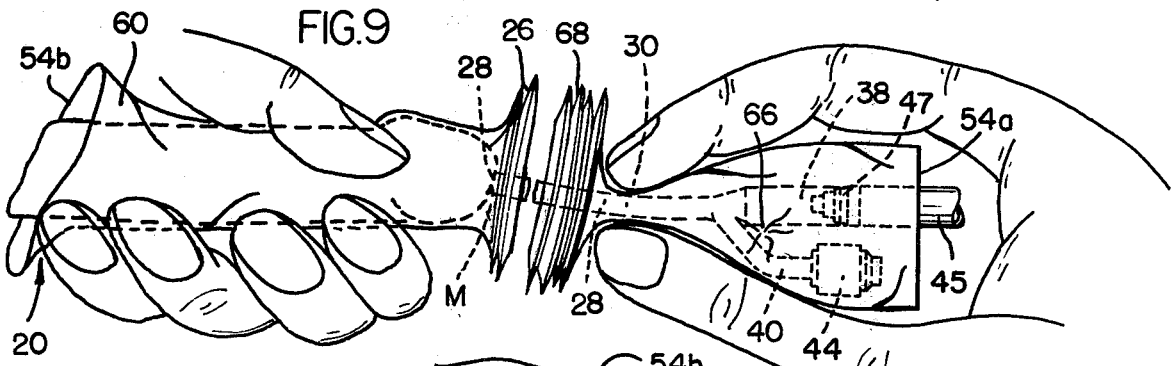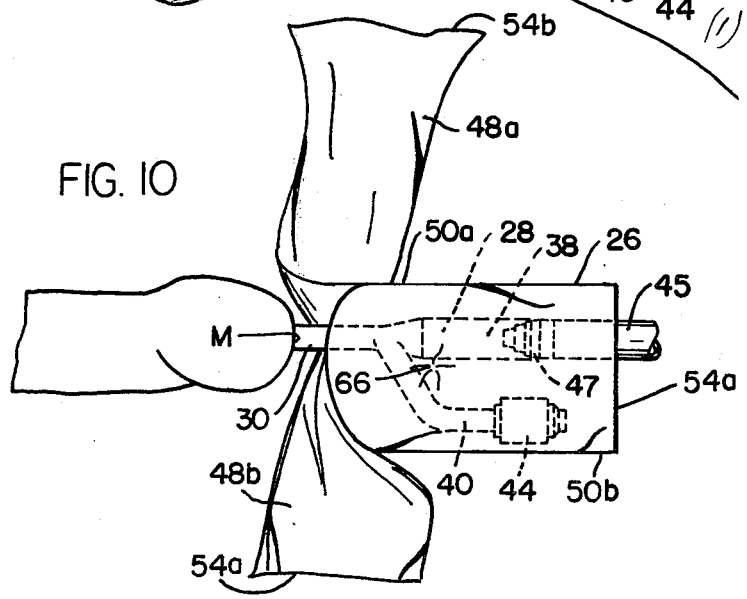

CATHETER ASSEMBLY

BACKGROUND OF THE INVENTION

The present invention relates to catheter assemblies, and more particularly to devices for placement of catheters.

A various assortment of catheters, such as urinary or Foley catheters, have been proposed for use on patients. In the case of Foley catheters, a distal end of the catheter shaft is inserted into the patient's urethra during placement, and the shaft is passed through the urethra until a balloon adjacent a distal end of the shaft is located in the bladder with a proximal end of the catheter located outside the patient's body. The balloon is then inflated in the bladder in order to retain the catheter in place, and during catheterization urine drains from the bladder through a drainage lumen in the catheter and through a drainage tube connected to the catheter into a drainage bag for collection therein.

Of course, it is necessary that the catheter should be placed in the patient without contamination of the catheter shaft, otherwise bacteria may be introduced into the bladder by the catheter with possible deleterious results to the patient. Additionally, it is desirable to lubricate the catheter shaft in order to facilitate passage of the shaft through the urethra. It is apparent that handling of the catheter during lubrication and placement significantly increases the likelihood that the cathether shaft may become contaminated, even handled through use of sterile gloves, since the gloves may become contaminated by inadvertent contact against the patient or other nonsterile object resulting in contamination of the catheter shaft when subsequently touched by the nonsterile gloves. In addition, it is desirable to eliminate the inconvenience caused by the physician by unnecessary placement of gloves and by the careful handling of the catheter required to prevent contamination of the gloves and catheter. As an alternative, devices have been proposed for the purpose of accomplishing lubrication and placement, but are unduly complex in structure and difficult in use.

SUMMARY OF THE INVENTION

A principal feature of the present invention is the provision of a catheter assembly of simplified structure to facilitate lubrication and placement of the catheter.

The catheter assembly comprises, a catheter having an elongated shaft, and an elongated sleeve of flexible material covering at least a substantial portion of the catheter. The sleeve has a pair of opposed first and second walls extending between a pair of opposed longitudinal fold lines at sides of the sleeve with the catheter being received between the walls in a generally flat configuration of the sleeve. The sleeve has a circumferential cuff of enlarged dimensions defining an open distal end of the sleeve, and the cuff is folded back along a lateral fold line over an adjacent portion of the sleeve.

A feature of the invention is that the sleeve may be grasped beneath the cuff and may be retained by the physician's hand without contamination of the catheter.

Another feature of the invention is that the distal end of the catheter may be readily lubricated while the sleeve is retained by the physician's hand without contamination of the catheter.

Yet another feature of the invention is that the cuff may be folded over the patient's body in a region surrounding the meatus, such that the surrounding region of the patient's body is covered by the cuff to prevent contamination of the catheter shaft.

Thus, a feature of the invention is that the catheter shaft may be readily passed through the urethra while the sleeve protects the catheter shaft and covers the body region surrounding the meatus.

Another feature of the invention is that the catheter may be aseptically placed in the patient's body without the use of sterile gloves.

Still another feature of the invention is that the walls of the sleeve are connected together intermediate a side arm and connector of the catheter in order to retain the catheter in place within the sleeve during placement of the catheter.

A feature of the invention is that the catheter assembly may be utilized to selectively place the catheter in a male or female patient.

Still another feature of the invention is that the sleeve includes opposed longitudinal lines of weakness, such that the walls may be severed and the sleeve may be readily removed from the catheter after placement.

Yet another feature of the invention is that the catheter may be preconnected to a drainage tube in the assembly.

Further features will become more fully apparent in the following description of the embodiments of this invention and from the appended claims.

DESCRIPTION OF THE DRAWINGS

In the drawings:

FIGS. 7-10 are fragmentary perspective views showing use of the sleeve during placement of the catheter in a patient.

DESCRIPTION OF THE PREFERRED EMBODIMENTS

Figure 1:
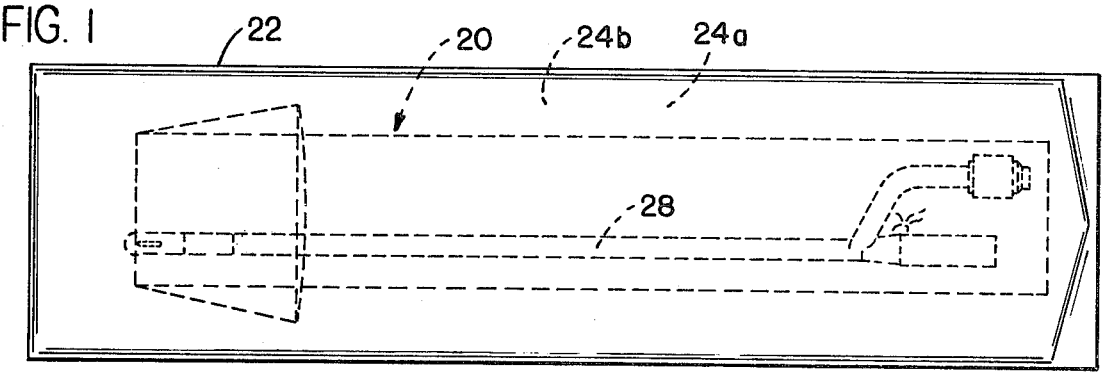
FIG. 1 is a plan view of a catheter assembly of the present invention as retained in a sterile package.

Referring now to FIG. 1, there is shown a sterile catheter assembly generally designated 20 which in one form is positioned within a closed sterile package 22 which maintains the assembly 20 in a sterile condition prior to use. The package 22 may have a pair of opposed side walls 24a and 24b with the assembly 20 being received between the side walls 24a and b, and with the side walls being sealed together around sides of the package 22. The side walls 24a and b may be peeled apart to provide access to the assembly 20 at the time of use.

With reference to FIGS. 2-5, the catheter assembly 20 comprises an elongated flexible sleeve or shield 26 of transparent plastic material, such as polyethylene or polyvinyl chloride, and a urinary or Foley catheter 28 received in a cavity 29 of the sleeve 26. The catheter 28 has an elongated shaft 30, a pair of drainage eyes 32 adjacent the distal end 34 of the shaft 30, a retention balloon 36 adjacent the distal end 34 of the catheter 28, a connector 38 extending from a proximal end of the shaft 30, a side arm 40 extending from the catheter 28 adjacent a proximal end 42 of the catheter 28, and a drainage lumen 43 extending from the drainage eyes 32 of the catheter through the shaft 30 to the proximal end 42 of the catheter 28. In one form, as shown, a drainage tube 45 is preconnected to the catheter 28 with an adapter 47 at the upstream end of the drainage tube 45 being received in the connector 38 at the proximal end 42 of the catheter 28. The drainage tube 45 communicates with a drainage bag (not shown), and the sleeve 36, catheter 28, preconnected drainage tube 45, and drainage bag are retained in a closed package larger than the package 22 in order to maintain the assembly in a sterile condition prior to use.

The normal placement procedure of the catheter 28 is described as follows. The distal end 34 of the catheter is inserted into the patient's urethra, and the catheter shaft 30 is passed through the urethra until the drainage eyes 32 and retention balloon 36 are located in the patient's bladder. Next, a syringe (not shown) is attached to a valve 44 on the catheter side arm 40, and fluid is pumped by the syringe through an inflation lumen 46 which communicates between the valve 44 and the retention balloon 36, such that the balloon 36 is inflated in the patient's bladder in order to retain the catheter 28 in place. Thus, urine drains through the drainage eyes 32, the drainage lumen 43, and the preconnected drainage tube 45 into the drainage bag for collection therein.

Figure 2:
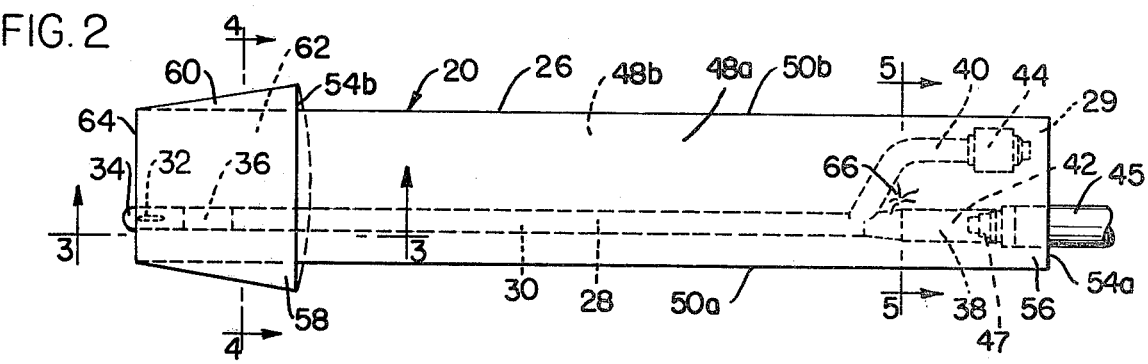
FIG. 2 is a plan view of the catheter assembly of FIG. 1.
Figure 3:
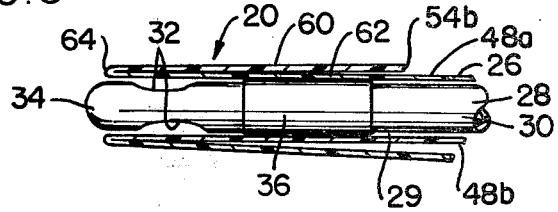
FIG. 3 is a fragmentary sectional view taken substantially as indicated along the line 3—3 of FIG. 2.
Figure 4:
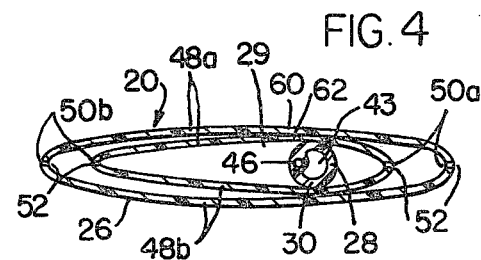
FIG. 4 is a sectional view taken substantially as indicated along the line 4—4 of FIG. 2.
Figure 5:
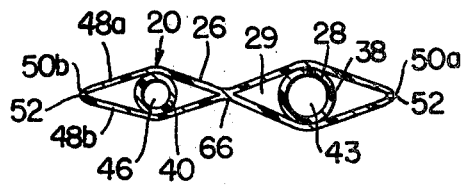
FIG. 5 is a sectional view taken substantially as indicated along the line 5—5 of FIG. 2.

The sleeve or sheath 26 comprises a pair of opposed first and second walls 48a and 48b extending between a pair of opposed longitudinally extending first and second fold lines 50a and 50b which define sides of the sleeve. As best shown in FIGS. 4 and 5, the fold lines 50a and b have perforations or heat seals 52 coincident with and extending the length of the fold lines 50a and b, such that the perforations 52 define lines of weakness at the location of the fold lines 50a and b. The sleeve 26 has an end edge 54a defining an open proximal end 56 of the sleeve 26, and a second edge 54b at the distal end of the sleeve when in an unfolded configuration. As shown, the sleeve 26 also has a circumferential cuff 60 extending from the end edge 54b, with the cuff 60 having enlarged dimensions relative the remainder of the sleeve 26. The sleeve 60 is folded over an adjacent portion 62 of the sleeve 26 along a lateral fold line 64 which defines a distal end of the folded sleeve. As best shown in FIGS. 2 and 5, the first and second walls 48a and b are connected together at a point 66 adjacent the juncture of and intermediate the catheter connector 38 and side arm 40. The connecting point 66 may be formed in a suitable manner, such as by heat sealing the walls together at the point 66. However, the connecting point 66 may be omitted for a urinary catheter not having a retention balloon and side arm.

As shown, the catheter 28 is received between the walls 48a and b of the sleeve with the sleeve in a generally flat configuration. The sleeve 26 covers the proximal end 38 of the catheter 28, while a distal end portion of the catheter is located adjacent an open end of the sleeve 26 defined at the lateral fold line 64.

Figure 6:
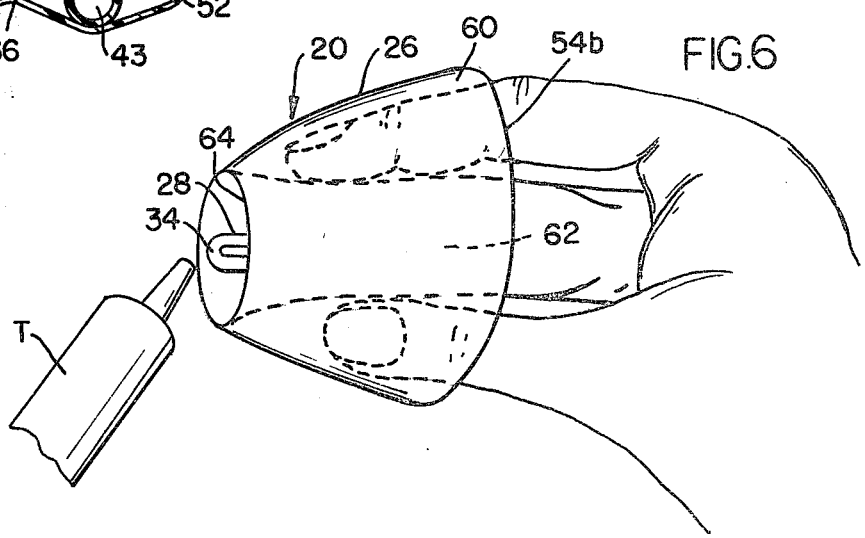
FIG. 6 is a fragmentary perspective view showing use of a sleeve during lubrication of a catheter in the assembly.

The use of the sleeve 26 during lubrication and placement of the catheter will be described in connection with FIGS. 6–10 as follows. Referring to FIG. 6, the sleeve 26 may be grasped by the physician's hand beneath the cuff 60 without the use of sterile gloves. Thus, the cuff 60 covers the physician's fingers and the sleeve protects the catheter from the contamination while being held preparatory to lubrication. Also, the connecting point 66 between the sleeve walls, previously discussed, maintains the catheter at the desired longitudinal position in the sleeve 26 with the distal end portion 34 of the catheter being exposed through the sleeve opening at fold line 64 in order to permit lubrication of the catheter distal end 34 by a suitable device, such as a tube T of lubrication jelly, as shown. In this manner, the catheter distal end may be readily lubricated in an aseptic manner to facilitate passage of the catheter shaft through the urethra without contamination.

As seen in FIG. 7, the distal end 34 of the lubricated catheter may be placed adjacent the meatus M of the patient while the cuff 60 covers the physician's fingers and the sleeve 26 prevents contamination of the catheter. As shown in FIG. 8, the cuff 60 is unfolded into a configuration covering the region of the patient surrounding the meatus M, and the cuff may be held in place by the other hand of the physician, such that the cuff provides a sterile barrier over the patient and catheter to prevent contact by the physician's hands against the catheter shaft and patient during placement of the catheter. Next, the distal end of the catheter may be inserted through the Meatus M into the urethra of the patient, and the catheter shaft may be passed through the urethra. Although the assembly is shown for use on a male patient, it will be apparent that the flexible cuff 60 of the sleeve 26 permits selective use of the assembly 20 on either a male or female patient, as desired.

The assembly is illustrated in FIG. 8 with the catheter shaft 30 having been partially passed into the patient's urethra. As shown, the sleeve may be folded together in a gathered portion 68 of the sleeve 26 to reduce the longitudinal dimensions of the sleeve during insertion of the catheter into the urethra. With reference to FIG. 9, the connecting point 66 between the opposed walls maintains the sleeve at the desired position on the catheter as the catheter shaft is passed further into the urethra while the sleeve 26 prevents contamination of the catheter shaft 30 by the physician's hand. When the catheter 28 has been fully passed through the urethra to the desired position for catheterization, the retention balloon may be inflated in the bladder. Next, as shown in FIG. 10, the sleeve 26 may be separated along the lines of weakness 50a and b in order to sever the sleeve walls and facilitate removal of the sleeve in an aseptic manner from the catheter 28 in spite that the catheter is connected to the drainage tube. When the fold lines have been severed to a location adjacent the connecting point 66, the connecting point 66 may be ruptured by further severance of the fold lines 50a and b, such that the sleeve 26 becomes completely separated into the individual walls 48a and b.

Thus, in accordance with the present invention, the protective sleeve permits lubrication and placement of the catheter in a convenient and simplified manner without the use of sterile gloves. In addition, the sleeve fully protects the catheter from contamination by the physician's hands during lubrication and placement of the catheter. Also, the sleeve may be readily separated and removed from the catheter and drainage tube after placement.

The foregoing detailed description is given for clearness of understanding only, and no unnecessary limitations should be understood therefrom, as modifications will be obvious to those skilled in the art.

We claim:

1. A catheter assembly, comprising:

a catheter having an elongated shaft;

an elongated sleeve of flexible material covering at least a substantial portion of said catheter, said sleeve having a pair of opposed first and second walls extending between a pair of opposed longitudinal fold lines at sides of the sleeve with said catheter being received between said walls in a generally flat configuration of the sleeve, said sleeve having a flexible circumferential cuff of enlarged dimensions defining an open distal end of the sleeve, said cuff being folded back along a lateral fold line over an adjacent portion of the sleeve, and said cuff being foldable distally during placement of the catheter.

2. The assembly of claim 1 wherein a distal end of the catheter is located adjacent a distal end of the sleeve.

3. The assembly of claim 1 wherein a proximal end of the sleeve is open.

4. The assembly of claim 1 wherein said catheter includes a connector and side arm extending from the shaft adjacent a proximal portion of the catheter, and in which the walls are secured together intermediate the catheter connector and side arm.

5. The assembly of claim 1 wherein said sleeve includes a line of weakness coincident with and extending substantially the length of at least one of said fold lines.

6. The assembly of claim 5 wherein said sleeve includes a line of weakness coincident with and extending substantially the length of the other of said fold lines.

7. The assembly of claim 6 wherein said weakness lines comprise lines of perforation in the sleeve.

8. The assembly of claim 1 including a package covering said sleeve and catheter.

9. The assembly of claim 1 wherein said sleeve is transparent.

10. The assembly of claim 1 including a drainage tube connected to a proximal end of the catheter.

11. A catheter assembly, comprising:

a urinary catheter having an elongated shaft, a side arm extending from the catheter adjacent a proximal end thereof, and a connector extending from a proximal end of the shaft; and an elongated sleeve of flexible transparent plastic material, said sleeve having a pair of opposed first and second walls extending between a pair of spaced longitudinally extending fold lines at opposed sides of the sleeve, said sleeve having a pair of weakness lines coincident with and extending substantially the length of said fold lines, said sleeve having a circumferential distal cuff of enlarged dimensions relative the remainder of the sleeve, said cuff being folded over an adjacent portion of the sleeve along a lateral fold line defining a distal end of the folded sleeve, said catheter being received between said walls in a generally flat configuration of the sleeve with a distal end of the catheter located adjacent said lateral fold line, said sleeve having an open proximal end, and said walls being connected together intermediate said catheter side arm and connector.

12. The assembly of claim 11 including a drainage tube connected to the proximal end of the catheter.

* * * * *

UNITED STATES PATENT AND TRADEMARK OFFICE
CERTIFICATE OF CORRECTION

PATENT NO. : 4,140,127
DATED : February 20, 1979
INVENTOR(S) : James P. Cianci and Frank K. Villari It is certified that error appears in the above-identified patent and that said Letters Patent are hereby corrected as shown below:

In column 1, line 36, after "caused" delete -- by -- .

In column 3, line 12, delete "36" and substitute -- 26 -- .

In column 3, line 68, delete second occurrence "the" .

In column 4, line 24, delete "Meatus" and substitute -- meatus -- .

Signed and Sealed this

Fifth Day of June 1979

[SEAL]

Attest:

RUTH C. MASON
Attesting Officer

DONALD W. BANNER
Commissioner of Patents and Trademarks